United States Patent [19]
Kamei et al.

[11] Patent Number: 5,220,033
[45] Date of Patent: Jun. 15, 1993

[54] SILOXANE COMPOUNDS AND THEIR PREPARATION

[75] Inventors: Masanao Kamei; Hiroshi Ohashi, both of Annaka, Japan

[73] Assignee: Shin-Etsu Chemical Co., Ltd., Tokyo, Japan

[21] Appl. No.: 713,228

[22] Filed: Jun. 11, 1991

[30] Foreign Application Priority Data

Jun. 13, 1990 [JP] Japan .................. 2-154706

[51] Int. Cl.$^5$ .............................. C07F 7/02
[52] U.S. Cl. .................................. 548/406
[58] Field of Search ......................... 548/406

[56] References Cited

U.S. PATENT DOCUMENTS

| | | | |
|---|---|---|---|
| 4,874,868 | 10/1989 | Bolich, Jr. | 548/406 |
| 5,081,260 | 1/1992 | Kubota et al. | 548/406 |
| 5,084,577 | 1/1993 | Bolich, Jr. | 548/406 |

FOREIGN PATENT DOCUMENTS

| | | | |
|---|---|---|---|
| 333432A | 9/1989 | European Pat. Off. | 548/406 |
| 52-42873 | 4/1977 | Japan | 548/406 |

*Primary Examiner*—Melvyn I. Marquis
*Assistant Examiner*—Karen A. Dean
*Attorney, Agent, or Firm*—Millen, White, Zelano & Branigan

[57] ABSTRACT

Novel siloxane compounds having N-alkylpyrrolidone incorporated therein as well as a reactive group such as amino, epoxy, acryl, methacryl, carboxyl, mercapt or carbinol group in their molecule possess the characteristics of both silicone and pyrrolidone and are highly water soluble. They are prepared by polymerizing an oligomer resulting from hydrolysis of a pyrrolidone-containing silicone, a cyclic siloxane, and a siloxane or by addition reacting an N-allylpyrrolidone to an organohydrogensiloxane. They are useful as fiber treating agents and cosmetic additives, and also effective for modifying various resins.

3 Claims, No Drawings

SILOXANE COMPOUNDS AND THEIR PREPARATION

This invention relates to novel siloxane compounds which are water soluble and useful in a wide variety of applications as fiber treating agents, cosmetic additives, and resin modifiers as well as a process for the preparation of such compounds.

BACKGROUND OF THE INVENTION

Known water soluble silicones are polyether silicones which are improved in water solubility by incorporating polyether into silicone backbones. Since the polyether silicones possess the characteristics of both silicone and polyether, they are useful as fiber treating agents capable of rendering fibers hydrophilic, soft and smooth as well as foam stabilizers for use in the preparation of expanded urethane due to their interfacial properties. They are also applicable to cosmetic compositions such as foundations and hair conditioners because of their physiological inertness, glazing and emulsifying ability.

Silicones having improved water solubility are useful in a variety of applications as indicated above. There is a need for the development of siloxane compounds which have higher water solubility and will find a wider variety of applications.

SUMMARY OF THE INVENTION

Therefore, an object of the present invention is to provide a new and improved siloxane compound having higher water solubility and finding a wider variety of applications. Another object of the present invention is to provide a process for preparing such a siloxane compound.

According to a first aspect of the present invention, there is provided a siloxane compound of the general compositional formula (1):

$$R^1_m R^2_n R^3_p SiO_{(4-m-n-p)/2} \tag{1}$$

wherein $R^1$ is a substituted or unsubstituted monovalent hydrocarbon group having 1 to 20 carbon atoms or a group represented by $-OR^4$ wherein $R^4$ is a hydrogen atom or a substituted or unsubstituted monovalent hydrocarbon group having 1 to 8 carbon atoms, $R^2$ is a group as defined for $R^1$ or a group of the following formula (2):

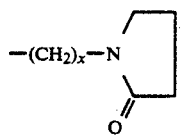

(2)

wherein x is an integer of 1 to 8, at least one of the $R^2$ groups being a group of formula (2), $R^3$ is an organic group containing an amino, epoxy, acryl, methacryl, carboxyl, mercapto, or carbinol group, and letters m, n, and p are in the range:

$0 < m < 2.2, 0 < n < 2.2, 0 < p < 2.2$, and $1.8 \leq m+n+p \leq 2.2$.

According to a second aspect of the invention, a siloxane compound of formula (1) is prepared by a process comprising the steps of:

hydrolyzing a compound of the general formula (3):

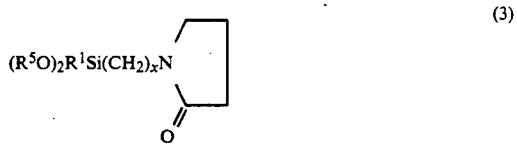

wherein $R^1$ is as defined above, $R^5$ is an alkyl group having 1 to 10 carbon atoms, and x is an integer of 1 to 8, to form an oligomer, and polymerizing the oligomer with a cyclic siloxane of the general formula (4):

wherein $R^1$ is as defined above and q is an integer of at least 3 and a siloxane of the general formula (5):

$$R^1_m R^3_p SiO_{(4-m-p)/2} \tag{5}$$

wherein $R^1$, $R^3$, m and p are as defined above.

According to a third aspect of the invention, a siloxane compound of formula (1) is prepared by a process comprising the step of:

addition reacting the vinyl group of an N-allylpyrrolidone of the general formula (7):

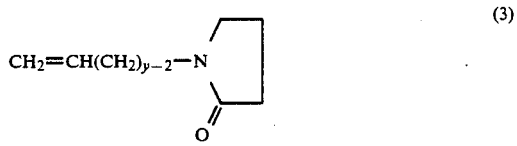

(3)

wherein y is an integer of 2 to 8, to the hydrogen atom of an organohydrogensiloxane of the general formula (6):

wherein $R^1$, m, n, and p are as defined above, $R^6$ is a group as defined for $R^1$ or a hydrogen atom, at least one of the $R_6$ groups being a hydrogen atom, and $R^7$ is an organic group containing an epoxy, acryl, methacryl or carbinol group.

Since the siloxane compounds of the present invention have N-alkylpyrrolidone incorporated therein so that the water solubility of pyrrolidone is imparted to the siloxane compounds, they possess the characteristics of both silicone and pyrrolidone. In addition, they have a reactive group such as an amino, epoxy, acryl, methacryl, carboxyl, mercapto and carbinol group in their molecule. These features ensure that they will find a wide variety of applications. More particularly, they are not only useful as fiber treating agents and cosmetic additives, but are also effective for modifying various resins such as general-purpose plastics, engineering plastics and semiconductor encapsulating materials.

DESCRIPTION OF THE PREFERRED EMBODIMENTS

The siloxane compounds of the present invention are siloxane compounds obtained by co-modifying N-alkylpyrrolidone and reactive groups and have the general compositional formula (1).

In formula (1), $R^1$ is a substituted or unsubstituted monovalent hydrocarbon group having 1 to 20 carbon atoms, preferably 1 to 3 carbon atoms or a group represented by $-OR^4$ wherein $R^4$ is hydrogen or a substituted or unsubstituted monovalent hydrocarbon group having 1 to 8 carbon atoms, preferably 1 to 3 carbon atoms. Illustrative examples of $R^1$ include monovalent hydrocarbon groups having 1 to 20 carbon atoms, for example, alkyl groups such as methyl, ethyl, butyl, dodecyl, and octadecyl groups, alkenyl groups such as vinyl and allyl groups, cycloalkyl groups such as cyclohexyl and cyclopentyl groups, aryl groups such as phenyl and naphthyl groups, and substituted ones of these groups in which some of the hydrogen atoms are replaced by halogen atoms, cyano group, nitro group or suitable organic groups. Illustrative examples of $-OR^4$ include hydroxyl, alkoxy, alkenyloxy, arloxy, and acyloxy groups while examples of $R^4$ groups include the substituted or unsubstituted $C_{1-8}$ hydrocarbon groups among the substituted or unsubstituted monovalent $C_{1-20}$ hydrocarbon groups illustrated for $R^1$.

$R^2$ is a group as defined for $R^1$ or a group of the following formula (2):

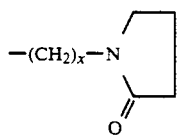

wherein x is an integer of 1 to 8, preferably 2 to 3. At least one of the $R^2$ groups is a group of formula (2). That is, the organopolysiloxane of formula (1) should contain at least one group of formula (2). The $R^2$ group preferably contains 10 to 80 mol %, more preferably 30 to 60 mol % of the group of formula (2).

$R^3$ is an organic group containing an amino, epoxy, acryl, methacryl, carboxyl, mercapto or carbinol group as a reactive group. Examples of $R^3$ are given below.

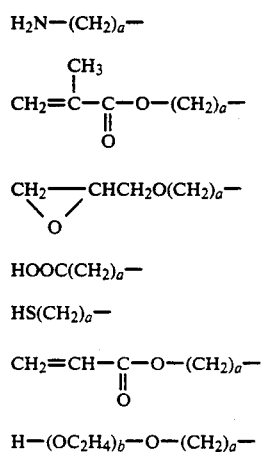

In the above formulae, a is an integer of 1 to 5, and b is an integer of 0 to 20.

Letters m, n, and p are in the range: $0 < m < 2.2$, $0 < n < 2.2$, $0 < p < 2.2$, and $1.8 \leq m+n+p \leq 2.2$. The preferred range is $0.8 < m < 1.2$, $0.1 < n < 0.7$, $0.3 < p < 1.2$, and $1.8 \leq m+n+p \leq 2.2$.

Several illustrative, non-limiting examples of the siloxane compound of formula (1) are given below.

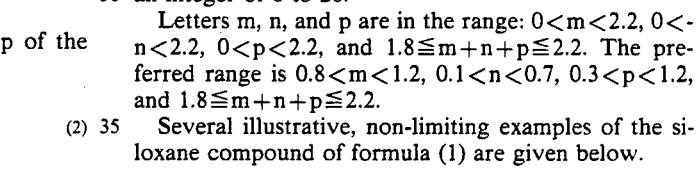

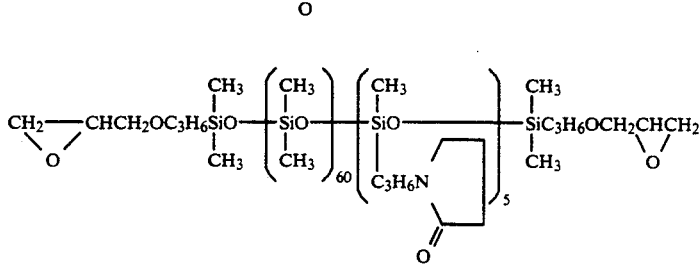

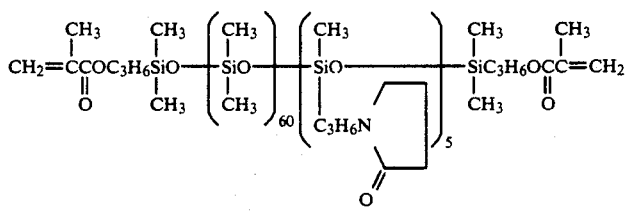

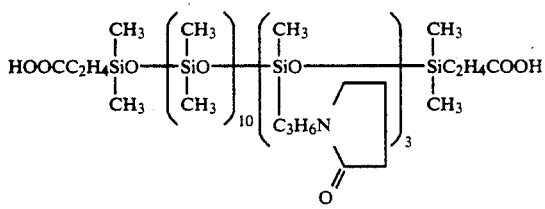

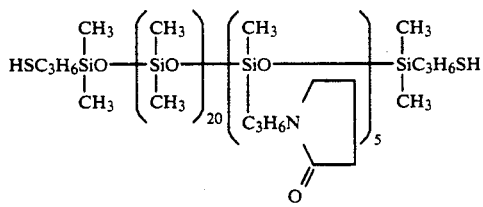

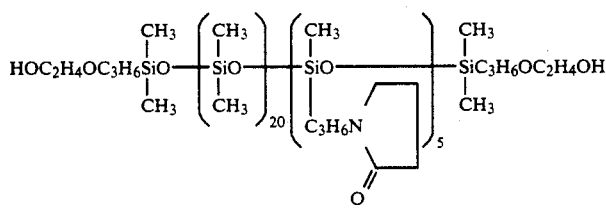

The siloxane compounds of formula (1) can be readily prepared by the following two processes.

The first process is to synthesize the siloxane compounds of formula (1) by hydrolyzing a compound of the general formula (3):

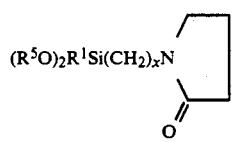
(3)

wherein $R^1$ is as defined above, $R^5$ is an alkyl group having 1 to 10 carbon atoms, preferably 1 to 3 carbon atoms, and x is an integer of 1 to 8, preferably 2 to 3 to form an oligomer, and polymerizing the oligomer with a cyclic siloxane of the general formula (4):

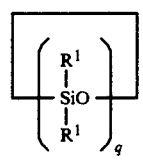
(4)

wherein $R^1$ is as defined above and q is an integer of at least 3, preferably 3 to 7, more preferably 3 to 5 and a siloxane of the general formula (5):

$R^1{}_m R^3{}_p SiO_{(4-m-p)/2}$  (5)

wherein $R^1$, $R^3$, m and p are as defined above.

The starting compound is of formula (3) wherein $R^5$ is an alkyl group having 1 to 10 carbon atoms, for example, methyl, ethyl, propyl, butyl and pentyl groups. Hydrolysis of the compound of formula (3) may be carried out in a conventional manner in the presence of an alkali or acid catalyst. The alkali catalysts include inorganic alkalis such as potassium hydroxide and sodium hydroxide and organic alkalis such as triethylamine and pyridine. The acid catalysts include hydrochloric acid, sulfuric acid, and nitric acid. The alkali or acid catalyst is used in a catalytic amount. Hydrolyzing conditions may be properly adjusted and usually include room temperature to 100° C., especially 60° to 80° C. and 1 to 3 hours.

At the end of hydrolysis, suitable solvent such as toluene, xylene, methanol, ethanol and the like is added to the reaction solution, from which an oligomer having units of formula (8) is obtained by stripping.

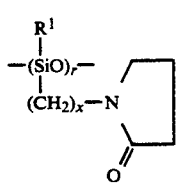
(8)

In formula (8), $R^1$ and x are as defined above, and r is usually 3 to 8. The process uses this oligomer as a first reactant.

The process uses as a second reactant a cyclic siloxane of formula (4):

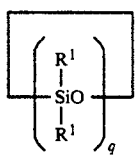
(4)

wherein $R^1$ is as defined above and q is an integer of at least 3, preferably 3 to 5. Examples of the cyclic siloxane of formula (4) include hexamethylcyclotrisiloxane and octamethylcyclotetrasiloxane.

The process uses as a third reactant a siloxane of formula (5):

$$R^1{}_m R^3{}_p SiO_{(4-m-p)/2} \qquad (5)$$

wherein $R^1$, $R^3$, m and p are as defined above. Examples of the siloxane of formula (5) are given below.

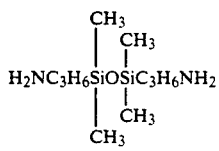

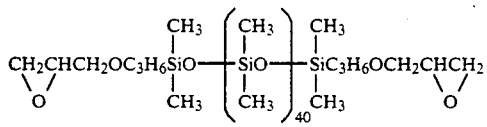

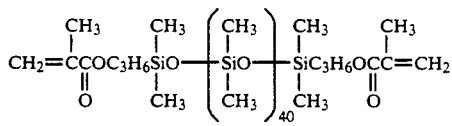

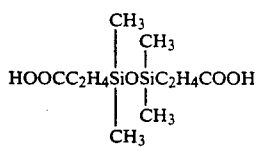

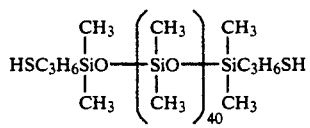

In the present process, the three reactants, the oligomer resulting from hydrolysis of a compound of formula (3), the cyclic siloxane of formula (4), and the siloxane of formula (5) are mixed for polymerization. Polymerization is preferably carried out in the presence of an alkali or acid catalyst. The alkali catalysts include cesium hydroxide, pottasium hydroxide, sodium hydroxide, and tetrabutyl phosphate, for example. One typical acid catalyst is trifluoromethanesulfonic acid and sulfuric acid. The alkali or acid catalyst is used in a catalytic amount. Polymerizing conditions may be properly adjusted and usually include room temperature to 150° C., especially 60 to 120° C. and 5 to 8 hours. At the end of reaction, the end product, siloxane compound of formula (1) can be isolated simply by stripping the reaction mixture in vacuum.

The second process is to synthesize the siloxane compounds of formula (1) by effecting addition reaction between an organohydrogensiloxane of the general formula (6):

$$R^1{}_m R^6{}_n R^7{}_p SiO_{(4-m-n-p)/2} \qquad (6)$$

wherein $R^1$, m, n, and p are as defined above, $R^6$ is a group as defined for $R^1$ or hydrogen at least one of the $R^6$ groups being hydrogen, and $R^7$ is an organic group containing an epoxy, acryl, methacryl or carbinol group and an N-allylpyrrolidone of the general formula (7):

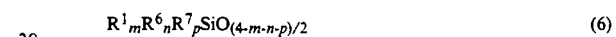
(7)

wherein y is an integer of 2 to 8. In this case, $R^6$ preferably contains 10 to 80 mol %, more preferably 30 to 60 mol % of hydrogen atom. In the reaction, the vinyl group of an N-allylpyrrolidone of formula (7) is addition reacted to the hydrogen atom of an organohydrogensiloxane of formula (6).

Examples of the organohydrogensiloxane of formula (6) are given below.

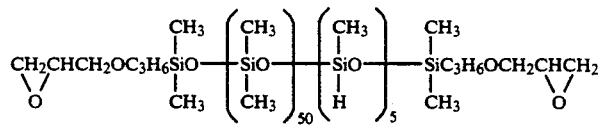

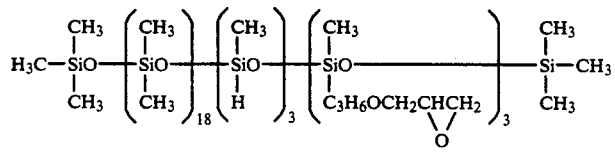

By the second process, a siloxane compound of the general compositional formula (1') is obtained.

$$R^1{}_m R^2{}_n R^7{}_p SiO_{(4-m-n-p)/2} \quad \ldots (1')$$

wherein $R^1$, $R^2$, $R^7$, m, n and p are as defined above.

In the second process, the organohydrogensiloxane of formula (6) and the N-allylpyrrolidone of formula (7) are used in such amounts that the molar ratio of the N-allylpyrrolidone of formula (7) to the hydrogen atom of the organohydrogensiloxane of formula (6) may range from 1:1 to 2:3.

Addition reaction is generally carried out in the presence of a catalytic amount of a catalyst. Examples of the addition reaction catalyst include platinum, palladium, and rhodium complexes.

Addition reaction may be carried out in either a solventless system or a solvent system. The solvents used herein are active hydrogen-free solvents, for example, aromatic hydrocarbons such as toluene and xylene, aliphatic hydrocarbons such as hexane and octane, esters such as ethyl acetate and butyl acetate, and chlorinated hydrocarbons such as carbon tetrachloride and trichloroethane. Reaction conditions may be properly adjusted and usually include room temperature to 150° C., especially 60 to 120° C. and 8 to 12 hours. The end of reaction can be determined simply by identifying the disappearance of the organohydrogensiloxane of formula (6) by infrared spectroscopy.

Since the siloxane compounds of the present invention possess the characteristics of both silicone and pyrrolidone, are highly water soluble, and have a reactive group in their molecule, they are not only useful as fiber treating agents and cosmetic additives, but are also effective for modifying various resins such as general-purpose plastics, engineering plastics and semiconductor encapsulating materials.

EXAMPLE

Examples of the present invention are given below by way of illustration and not by way of limitation.

EXAMPLE 1

A 1-liter flask equipped with a stirrer and condenser was charged with 300 grams of 3-(2-oxy-1-pyrrolidyl)-propylmethyldiethoxysilane of the following formula.

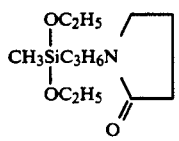

To the flask was added 0.05 grams of 35% hydrochloric acid. Using an oil bath, the flask was heated to an interior temperature of 60° C. With stirring, 100 grams of water was added dropwise and hydrolysis effected at 80° C. for two hours. At the end of reaction, 100 grams of toluene was added. By stripping the mixture at 100° C. in vacuum, there was obtained 195 grams of a pyrrolidone polymer of the following formula.

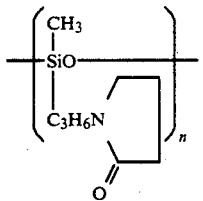

Next, a 200-ml flask was charged with 46.3 grams of the pyrrolidone polymer, 37.0 grams of octamethyltetrasiloxane, and 12.4 grams of an aminosiloxane of the following formula and heated to 110° C.

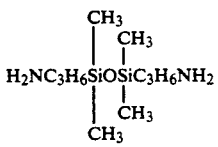

To the flask was added 0.29 grams of tetrabutyl phosphate. Polymerization was effected at 110° to 120° C. for 5 hours. The reaction mixture was stirred at 150° C. for a further 2 hours and then stripped at 130° C. in vacuum, obtaining 81 grams of a polysiloxane of the following formula.

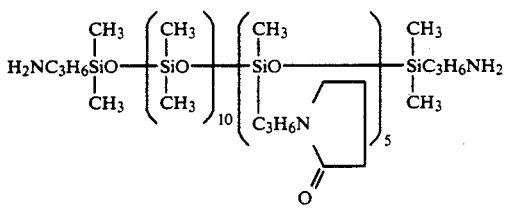

The polysiloxane had an amine equivalent of 951 g/mol (theory 956 g/mol). It was analyzed by gel permeation chromatography (GPC) with the following results.

Number average molecular weight (Mn) calculated based on polystyrene: 1900

Weight average molecular weight (Mw) calculated based on polystyrene: 3480

Polydispersion: Mw/Mn=1.82

Nitrogen analysis: 5.06% (theory 5.12%)

EXAMPLE 2

A 500-ml flask was charged with 46 grams of the pyrrolidone polymer obtained in Example 1, 74 grams of octamethyltetrasiloxane, and 165 grams of an epoxy-modified silicone of the following formula and heated to 110° C.

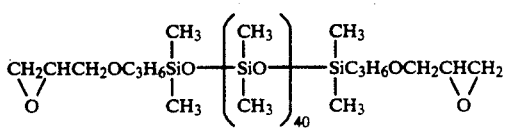

To the flask was added 0.85 grams of tetrabutyl phosphate. Polymerization was effected at 110° to 120° C. for 5 hours. The reaction mixture was stirred at 150° C. for a further 2 hours and then stripped at 130° C. in vacuum, obtaining 241 grams of a polysiloxane of the following formula.

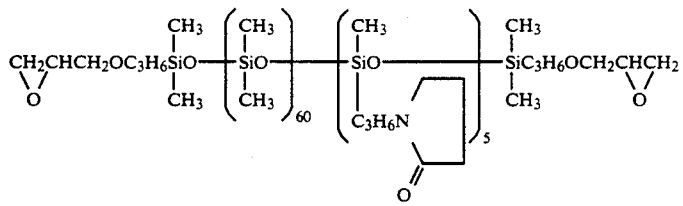

The polysiloxane had an epoxy equivalent of 2895 g/mol (theory 2852 g/mol). Its GPC results are shown below.
  Number average molecular weight (Mn) calculated based on polystyrene: 5600
  Weight average molecular weight (Mw) calculated based on polystyrene: 9950
  Polydispersion: Mw/Mn = 1.78
  Nitrogen analysis: 1.19% (theory 1.22%)

EXAMPLE 3

A 300-ml flask was charged with 27.8 grams of the pyrrolidone polymer obtained in Example 1, 44.4 grams of octamethyltetrasiloxane, and 100 grams of a methacryl-modified silicone of the following formula and heated to 110° C.

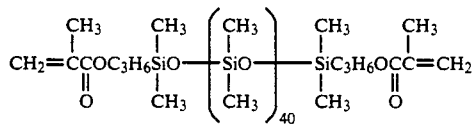

To the flask was added 0.52 grams of tetrabutyl phosphate. Polymerization was effected at 110° to 120° C. for 5 hours. The reaction mixture was stirred at 150° C. for a further 2 hours and then stripped at 130° C. in vacuum, obtaining 142 grams of a polysiloxane of the following formula.

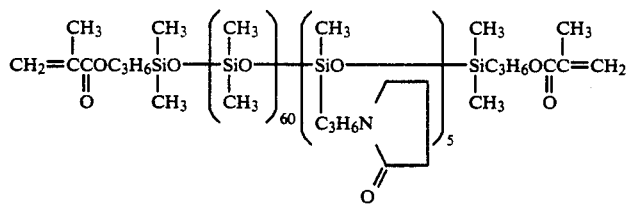

The polysiloxane was analyzed by GPC with the following results.
  Number average molecular weight (Mn) calculated based on polystyrene: 6000
  Weight average molecular weight (Mw) calculated based on polystyrene: 10020
  Polydispersion: Mw/Mn = 1.67
  Nitrogen analysis: 1.26% (theory 1.22%)

EXAMPLE 4

A 300-ml flask was charged with 27.8 grams of the pyrrolidone polymer obtained in Example 1, 44.4 grams of octamethyltetrasiloxane, and 97.3 grams of a mercapto-modified silicone of the following formula and heated to 60° C.

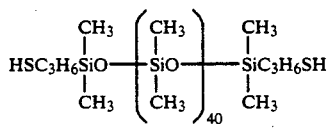

To the flask was added 0.50 grams of trifluoromethanesulfonic acid. Polymerization was effected for 8 hours. The reaction solution was cooled down and mixed with 0.25 grams of water by agitation. Further, 50 grams of sodium bicarbonate and 50 grams of sodium sulfate were added thereto. The mixture was agitated for 3 hours, filtered, heated at 110° C., and stripped in vacuum. There was obtained 139 grams of a polysiloxane of the following formula.

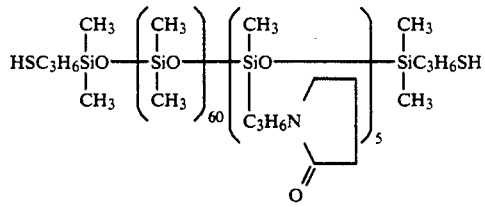

The polysiloxane was analyzed by GPC with the following results.
  Number average molecular weight (Mn) calculated based on polystyrene: 5500
  Weight average molecular weight (Mw) calculated based on polystyrene: 10800
  Polydispersion: Mw/Mn = 1.91
  Nitrogen analysis: 1.14% (theory 1.24%)

EXAMPLE 5

A 500-ml flask equipped with a stirrer and condenser was charged with 217 grams of organohydrogenpolysiloxane of the following average formula.

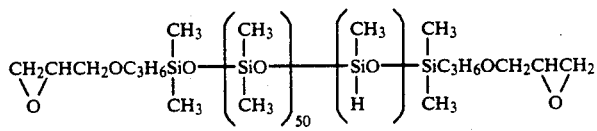

To the flask was added 0.15 grams of 2% chloroplatinic acid in isopropyl alcohol. Using an oil bath, the flask was heated to an interior temperature of 90° C. With stirring, 39 grams of N-allylpyrrolidone was added dropwise and reaction effected at 110° C. over 10 hours. After the substantial disappearance of Si—H bond was observed, the reaction mixture was stripped at 110° C. in vacuum, obtaining 223 grams of an organopolysiloxane of the following formula.

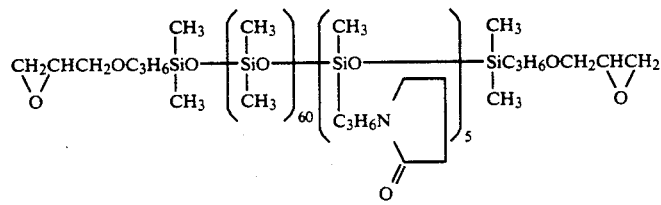

The organopolysiloxane had an epoxy equivalent of 2503 g/mol (theory 2482 g/mol). Its GPC results are shown below.

Number average molecular weight (Mn) calculated based on polystyrene: 4400
Weight average molecular weight (Mw) calculated based on polystyrene: 7480
Polydispersion: Mw/Mn=1.70
Nitrogen analysis: 1.43% (theory 1.37%)

Although some preferred embodiments have been described, many modifications and variations may be made thereto in the light of the above teachings. It is therefore to be understood that within the scope of the appended claims, the invention may be practiced otherwise than as specifically described.

We claim:

1. A siloxane compound of the compositional formula (1):

$$R^1{}_m R^2{}_n R^3{}_p SiO_{(4-m-n-p)/2} \qquad (1)$$

wherein $R^1$ is a substituted or unsubstituted monovalent hydrocarbon group having 1 to 20 carbon atoms or a group represented by -$OR^4$ wherein $R^4$ is a hydrogen or a substituted or unsubstituted monovalent hydrocarbon group having 1 to 8 carbon atoms, $R^2$ is a group as defined for $R^1$ or a group of the following formula (2):

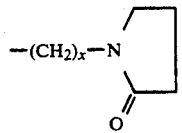

wherein x is an integer of 1 to 8, at least one of the $R^2$ groups being a group of formula (2), $R^3$ is an organic group containing an amino, epoxy, acryl, methacryl, carboxyl, mercapto or carbinol group, and letters m, n, and p are in the range:

$0 < m < 2.2, 0 < n < 2.2, 0 < p < 2.2$, and $1.8 \leq m+n+p \leq 2.2$.

2. The siloxane compound of claim 1, wherein $R^3$ is selected from the group consisting of:

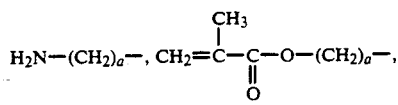

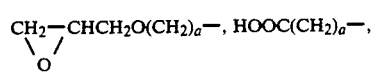

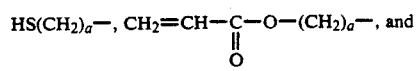

wherein a is an integer of 1 to 5 and b is an integer of 0 to 20.

3. The siloxane compound of claim 1, wherein the letters m, n and p are in the range $0.8 < m < 1.2$, $0.1 < n < 0.7$ and $0.3 < p < 1.2$.

* * * * *